(12) United States Patent
Kampouris et al.

(10) Patent No.: US 8,785,204 B2
(45) Date of Patent: Jul. 22, 2014

(54) METHODS OF ASSAYING FOR TETRAHYDROCANNABINOL

(75) Inventors: Dimitrios Konstantinos Kampouris, Nottingham (GB); Patrick Robinson Huddleston, Nottingham (GB); Craig Edward Banks, Nottingham (GB)

(73) Assignee: Oxtox Limited, Stockport (GB)

( * ) Notice: Subject to any disclaimer, the term of this patent is extended or adjusted under 35 U.S.C. 154(b) by 16 days.

(21) Appl. No.: 13/201,446

(22) PCT Filed: Jan. 28, 2010

(86) PCT No.: PCT/GB2010/000137
§ 371 (c)(1),
(2), (4) Date: Dec. 19, 2011

(87) PCT Pub. No.: WO2010/092322
PCT Pub. Date: Aug. 19, 2010

(65) Prior Publication Data
US 2012/0122229 A1 May 17, 2012

(30) Foreign Application Priority Data
Feb. 13, 2009 (GB) .................................. 0902493.6

(51) Int. Cl.
G01N 33/94 (2006.01)
G01N 27/00 (2006.01)

(52) U.S. Cl.
USPC .................. 436/93; 436/63; 436/96; 436/98; 436/106; 436/111; 436/128; 436/131; 436/149; 436/150

(58) Field of Classification Search
USPC ........... 436/63, 91, 93, 96, 98, 106, 111, 127, 436/128, 131, 149, 150, 901; 422/430, 422/82.01, 82.02, 554; 435/4, 29
See application file for complete search history.

(56) References Cited

U.S. PATENT DOCUMENTS 5,834,171 A * 11/1998 Suzuki et al. .................. 430/465
2006/0014302 A1 * 1/2006 Martinez et al. .............. 436/518
2009/0263468 A1 * 10/2009 McAnulty et al. ............ 424/443

FOREIGN PATENT DOCUMENTS

WO 2006134386 A1 12/2006

OTHER PUBLICATIONS

Fiamegos et al. Analytical Chimica Acta, vol. 403, 2000, pp. 315-323.*
Svobodova, D.; "Color reaction of phenols with 4-aminoantipyrine" Mikrochimica ACTA, pp. 384-390, Coden: Miacaq 1971.
Ettinger, M. B. et al.; "Sensitive 4-aminoantipyrine method for phenolic compounds", Anal. Chem., 23, pp. 1783-1788, Coden: Ancham, 1951.
Goodwin Alexander et al; "Graphite micropowder modified with 4-amino-2, 6-diphenylphenol supported on basal plane pyrolytic graphite electrodes; Micro sensing platforms for the indirect electrochemical detection of Delta(9)-tetrahydrocannabinol in saliva" Electroanalysis, VHC Publishers, Inc., US, vol. 18, No. 11, Jun. 1, 2006, pp. 1063-1067.
European Patent Office, "International Search Report and Written Opinion", PCT/GB2010/000137, Mar. 30, 2010.

* cited by examiner

Primary Examiner — Maureen Wallenhorst
(74) Attorney, Agent, or Firm — IPHorgan Ltd.

(57) ABSTRACT

The invention provides a method of assaying for tetrahydrocannabinol in a body fluid. The method includes contacting a sample of body fluid with an imine capable of reacting with tetrahydrocannabinol to yield a quinone imine, and detecting the formation of a quinone imine, where the sample is contacted with the reagent compound at a pH of at least 10.5.

10 Claims, 5 Drawing Sheets

METHODS OF ASSAYING FOR TETRAHYDROCANNABINOL

Figure 1:
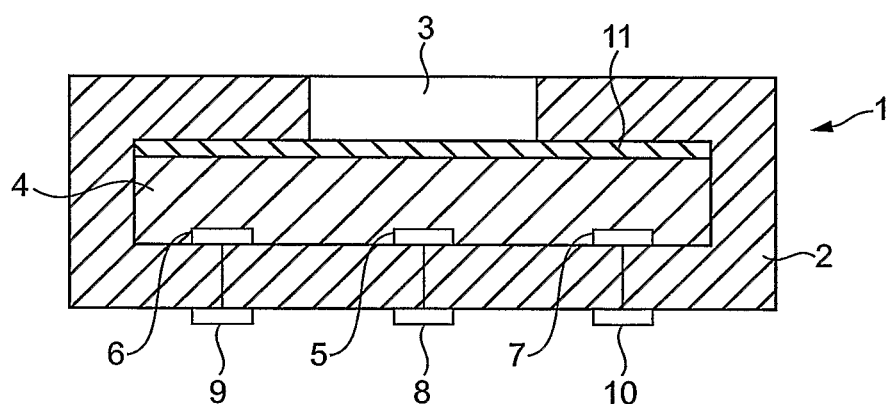

This invention relates to improvements in and relating to methods of assaying for tetrahydrocannabinol in body fluids, and to kits and cartridges for use in such methods.

Tetrahydrocannabinol (THC) is the active component in cannabis.

Cannabis consumption, e.g. by smoking or eating, can lead to reduced performance capacity and can cause risk to the user and others where for example the user operates a machine, for example drives an automobile, while under the influence. There is thus a need for simple non-invasive assays for THC, for example for use by traffic police.

THC is a phenol and electrochemical assays for phenols in body fluids are described for example in WO2006/134386, the contents of which are hereby incorporated by reference. In the assay method described in WO2006/134386, the sample to be tested is brought into contact with a reagent compound having two redox forms, one of which can react to bond covalently to the phenol. By cycling a voltage across the sample and detecting the current through the sample, the presence of a phenol in the sample is revealed by depletion of the current due to the sequestering of the reagent compound by phenol binding.

For any assay used for screening it is important that the occurrence of false positive results is minimised. The assay described in WO2006/134386 does not discriminate between phenols, and since phenols may legitimately be present in a body fluid sample, for example the polyphenols such as epigallocatechin-3-gallate (EGCG) that are present in tea and red wine, there is a need for an assay with less propensity to yield false positive results.

We have now surprisingly found that in assays for THC in body fluids which involve reaction of THC with an imine to produce a quinone imine, the occurrence of false positive results may be reduced by performing the reaction at a pH of at least 10.5.

Thus viewed from one aspect the invention provides a method of assaying for tetrahydrocannabinol in a body fluid, said method comprising contacting a sample of body fluid with an imine capable of reacting with tetrahydrocannabinol to yield a quinone imine, and detecting the formation of a quinone imine, characterised in that said sample is contacted with said reagent compound at a pH of at least 10.5, preferably 10.5 to 14, especially at least 10.8, more especially 10.8 to 12, particularly about 11.0.

In the assay method of the invention, the body fluid sample may be of any body fluid, e.g. blood, mucus, urine or saliva, preferably urine or saliva and most preferably saliva. Before being contacted with the imine, the sample may be treated, for example to add a reference compound also reactive with the imine, to remove macromolecular material, to remove cells, to adjust pH, etc. Particularly preferably the sample is adjusted to the desired pH before or on being contacted with the imine.

The imine may be used as such, or alternatively a compound transformable into an imine, e.g. by oxidation, may be used and may be transformed into an imine as part of the assay method. Such an imine precursor will conveniently be a compound having two redox forms, one of which is an amine, the other the imine.

Typically, the imine will be a compound in which the imine nitrogen is attached to a carbon atom of a delocalised electron system, preferably one containing at least one further carbon atom. Preferably, the imine is a compound of formula I

where Q is —O—, —S—, =N— or —NR'—; each R', which may be the same or different, is H or an electron-withdrawing or -donating group; X* is N* or C*; n is 0 or 1; and * indicates that the carbons or nitrogens are part of a delocalised electron system. Such compounds will react with a phenol such as THC to form a quinone imine.

In one preferred embodiment, an imine precursor is used which may be converted to an imine by oxidation, e.g. an amine of formula II

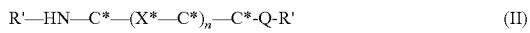

where Q, R', n, X* and * are as defined above.

Alternatively, the imine precursor may be a cyclic hydrazide such as maleic hydrazide which ring opens on oxidation to form an imine.

The group $C^*(X^*C^*)_n C^*$ preferably forms part of an unsaturated ring, e.g. an aromatic ring, itself optionally substituted or fused to another ring. Such unsaturated ring systems include benzene, pyridine, pyrimidine and pyrazolone rings for example.

The imine precursor is preferably selected from 1-(substituted-amino)-4-amino benzenes, 1-(substituted-amino)-4-hydroxy-benzenes, 1-(substituted-amino)-2-amino-benzenes, 1-(substituted-amino)-2-hydroxy-benzenes, 1,4-di(substituted-amino)-benzenes, 1,2-di(substituted-amino)-benzenes. 2,3-diaminopyridines, 2,5-diaminopyridines, 3,4-diaminopyridines, 2-amino-3-hydroxypyridines, 4,5-diaminopyrimidines, 4-aminopyrazolones and maleic hydrazides and substituted derivatives thereof, e.g. substituted to introduce electron-withdrawing or -donating groups affecting the delocalised electron system or to provide groups for attachment of the compound to a substrate.

Electron-withdrawing or -donating groups may be used to modify the activity of the imine towards THC with electron-donating groups, which will generally be preferred, serving to reduce reactivity. Electron-withdrawing or -donating is of course judged relative to hydrogen. Examples of typical such groups include halogen (e.g. Cl), acyl (e.g. $CH_3CO$), aryl (e.g. phenyl), alkyl, alkenyl, aralkyl, etc. Preferably any R' group contains up to 20 carbons, especially up to 12 carbon atoms and optionally is substituted with a functional group by which it may be bound, covalently or non-covalently, to a substrate, e.g. thiol, hydroxyl, carboxyl, vinyl, or diazonium groups. Such functional groups, while preferably present in a group NHR' in a precursor of formula II may additionally or alternatively be present as or on substituents at the remaining skeletal positions of the compound, e.g. the C* carbons.

The groups R' may be introduced onto the otherwise unsubstituted compound by conventional chemical reactions, optionally preceded by protection of groups where R' substitution is undesired and followed by cleavage of the protecting groups. Thus for example an acetyl group may be introduced by reaction of the primary amine with acetyl chloride.

As mentioned above, the group of structure II is preferably part of an aromatic ring. Examples of suitable substituents on the carbons of the aromatic ring are given in WO2006/134386. As indicated above, such substituents may include functional groups for attachment to a substrate as mentioned above.

Detection of the quinone imine may be by any convenient method. Electrochemical detection and detection by absorption, emission or scattering of light are particularly preferred as they are readily effected outside the laboratory, e.g. at the roadside.

Electrochemical detection may be effected by exposing the sample to an applied voltage, preferably a cycled voltage, and determining the resultant current. Where electrochemical detection is used, it is particularly preferred to have the imine or imine-precursor bound to, coated on, or impregnated within the working electrode. The electrochemical detection techniques described in WO2008/003999 and WO2006/134386, particularly cyclic voltammetry, may conveniently be used.

Before quinone imine detection is effected, the sample is preferably incubated with the imine or imine precursor for a preset period, for example 1 to 20 minutes, preferably 2 to 10 minutes, e.g. 3-5 minutes.

The pH of the sample may conveniently be maintained at the desired level by addition of a base or, more preferably, a buffer. This may be added to the sample before it is contacted with the imine, or more preferably it may be present with the imine or imine precursor. Thus in one particularly preferred embodiment the sample is applied to a porous substrate which is impregnated with imine or imine precursor and a buffer. In another preferred embodiment, where electrochemical detection is to be carried out, electrodes are positioned adjacent a porous substrate such that current may flow through the substrate when moist. In this embodiment, the imine or imine precursor may be impregnated into the substrate or may be bound to or impregnated into the working electrode. Here again a buffer may be impregnated into the substrate or may be bound to or impregnated into the working electrode. Alternatively, an alkaline material, e.g. sodium or potassium hydroxide, may be incorporated into the electrode material.

Where electrochemical detection is used, the conversion of an imine precursor to the active imine form may occur on application of an electric potential. Otherwise where an imine precursor is used an oxidising agent or other imine precursor activator may also be contacted with the sample. Such an activator may for example be impregnated into a porous substrate to which the sample is to be applied.

As mentioned above, the assay method of the invention is especially suited for use out of the laboratory. Accordingly, it is preferred that the operator be provided with a test kit, preferably one comprising imine or imine precursor containing cartridges which can be loaded with the sample and, if necessary a separate detector which can be used to read the loaded cartridges.

Thus viewed from a further aspect the invention provides a kit comprising an imine or imine precursor, optionally a buffer, optionally an absorbent pad, optionally a quinone imine detector, and optionally instructions for performance of a method according to the invention.

Viewed from a still further aspect the invention provides an assay cartridge comprising a casing having an aperture for placement of a body fluid sample and containing a water-absorbent pad, an imine or imine precursor, and a buffer.

The cartridge preferably is provided packed in a water-tight container, e.g. a foil sachet, to prevent degradation before use. The cartridge is conveniently in the form of a stick, plate or tablet to allow easy insertion into a quinone imine detector.

If, as is preferred, detection is to be by electrochemical means, the cartridge preferably also is provided with electrodes positioned to be in electrical contact with the pad when the latter is wet and with electrical contacts which, when the cartridge is placed in a detector, will allow a voltage to be applied in the wet pad from an electrical source in the detector. While no electrodes are strictly necessary within the cartridge as electrodes in the detector may be brought into contact with the wet pad when it is inserted within the detector, it is preferred that three electrodes be present, a working electrode, a counter-electrode and a reference electrode. These may be of any conventional material; however it is preferred that the working electrode be a carbon-based electrode. In the case where electrodes are present, the imine or imine precursor is preferably bound to, coated upon or impregnated into the working electrode. The buffer may be positioned similarly or impregnated into the pad.

Where detection is to be by radiation emission, scattering or absorbance, the cartridge preferably has an aperture or radiation-translucent window allowing radiation from the pad to be detected.

In order to reduce the likelihood of cross reactions with large biomolecules present in the sample, e.g. proteins, the cartridge is preferably provided with a semi-permeable membrane covering the surface of the pad to which the sample is applied and which is permeable to THC. The membrane may be for example of cellulose acetate. Where radiation from the pad is to be detected, then either this membrane should be translucent to the relevant wavelengths or a separate window or aperture to the pad should be provided.

Detection may be quantitative, semi-quantitative or qualitative, for example giving a value for THC concentration in the body fluid or an indication as to whether the THC concentration is above or below one or more pre-set values. Desirably, the detector will have a display to allow the operator to see the detected "value". Also desirably, the detector will record the detected value and the identity of the cartridge. Cartridge identity can be determined by coding the surface of the cartridge in a manner readable by the detector, e.g. using a bar code or the like.

The assay method of the invention will generally involve calibration of the selected reagents and detection techniques using standards, i.e. aqueous samples containing known concentrations of THC. The calibration values may also be encoded into the cartridge identification so that there is no batch-to-batch variation when cartridges of different batches are read with the same detector.

The detector will preferably also include a timer so that the sample is incubated for the desired time period before a detected "value" is presented to the operator.

In a particularly preferred embodiment of the invention, a dual assay is performed with the sample being contacted with the imine at least two pHs, one above 10.5 and the other below 9.0, preferably below 8.0, e.g. 5.0 to 8.0, particularly 6.0 to 7.5, especially about 7.0. Such a dual assay may be performed as two separate assays or, more preferably, by applying the sample to two sections of porous substrate or to a single section of porous substrate with differently buffered regions. In this way a positive result for phenols at the lower pH value will alert the operator to the presence of phenols other than THC, for example the polyphenols found in tea or red wine. In the event of a positive result at both low and high pH, the test subject could be asked to provide a further sample for laboratory verification of the presence of THC to avoid the high pH positive result being challenged in court.

The occurrence of false positive results may be further reduced by detecting the quinone imine at two or more different wavelengths or voltages. The occurrence of false negatives can be reduced by inclusion of a further reagent which is detectable on correct operation of the method, e.g. a material which undergoes a redox reaction at a different voltage or which releases a fluorescent material on incubation with an aqueous sample.

The use of 4-amino-pyrazolones as reagents in the detection of phenols, such as for example THC, is itself new and forms a further aspect of the present invention. Viewed from this aspect the invention provides a method of assaying for a phenol analyte in a body fluid sample, said method comprising contacting said sample with a 4-imino-pyrazolone and detecting any resulting quinone imine.

In this method, the 4-imino-pyrazolone may be generated in situ by oxidation of a 4-amino-pyrazolone, e.g. by the use of an oxidizing agent such as for example ferricyanide or hydrogen peroxide.

The 4-amino-pyrazolone may if desired carry substituents on the ring carbons and nitrogens, e.g. electron-donating or withdrawing substituents to modify the rate of reaction of the imino-pyrazolone with the phenol, or substituents which can bind to a substrate in order that the reagent be substrate bound. Where quinone imine detection is electrochemical, it is particularly desired that the 4-amino-pyrazolone be coupled to the working electrode.

The substituents on the pyrazolone ring may be any substituents that still permit the quinone imine to form. Particularly preferred are alkyl and aryl groups, optionally substituted for example by amino or alkoxy groups. Such alkyl groups preferably contain 1 to 6 carbons, especially 1 or two carbons. The aryl groups preferably are phenyl groups. Examples of particular 4-amino-pyrazolones that may be used include 4-aminoantipyrine, 4-amino-2-(p-amino-phenyl)-1-methyl-pyrazol-3-one, 4-amino-1-ethyl-5-methyl-1,2-dihydro-3H-pyrazol-3-one, 4-amino-5-(p-amino-phenyl)-1-methyl-2-phenyl-1,2-dihydro-3H-pyrazol-3-one, 4-amino-2-(p-amino-phenyl)-1-methyl-5-phenyl-1,2-dihydro-3H-pyrazol-3-one, 4-amino-5-methyl-1,2-diphenyl-1,2-dihydro-3H-pyrazol-3-one, 4-amino-1-methyl-2,5-diphenyl-1,2-dihydro-3H-pyrazol-3-one, and 4-amino-5-(p-methoxy-phenyl)-1-methyl-2-phenyl-1,2-dihydro-3H-pyrazol-3-one.

Substituted 4-amino-pyrazolones may be prepared in a four-step procedure: form a hydrazone by condensing $X-C_6H_4NHNH_2$ with $EtOCOCH_2COR$ and directly cyclise to form the pyrazolone ring; N-alkylate; nitrate; and reduce the nitro group to an amine.

As described earlier, quinone imine detection may be by any convenient method; however electrochemical detection is preferred.

Certain embodiments of the method and cartridges of the invention will now be described in the following non-limiting Examples and with reference to the accompanying drawings, in which:

FIG. 1 is a schematic cross section through a cartridge according to the invention for electrochemical reading; and FIGS. 2 to 5 are voltammograms.

Referring to FIG. 1 there is shown a cartridge 1 having a plastics casing 2 with an aperture 3 for saliva application and containing a cellulosic pad 4 impregnated with a buffer. Below pad 4 are disposed three electrodes, a working electrode 5, a counter-electrode 6 and a reference electrode 7. Each electrode is coupled by a wire to a contact plate (8, 9 and 10) on the outside of the case. Working electrode 5 is a carbon electrode coated with an imine precursor. The surface of pad 4 adjacent aperture 3 is covered by a semi-permeable cellulose acetate membrane 11.

In use, the cartridge is removed from its wrapper (not shown), a saliva sample is applied to aperture 3, the cartridge is inserted into a detector causing contact plates 8, 9 and 10 to come into contact with corresponding contacts in the detector and a timer in the detector to start. After the preset incubation time, a voltage is cycled across electrodes 5 and 6, the current values at two preset voltages are determined and compared with calibration data, and a value for the THC content of the saliva sample is displayed.

EXAMPLE 1

Detection of THC 1 mM aqueous solutions of 4-aminoantipyrine (4-AAP), an imine precursor, were prepared from a 20 mM solution of 4-AAP in methanol using 0.05M phosphate buffered saline pH 11.0 and 0.1 M phosphate buffered saline pH 7.0. Delta-9-tetrahydrocannabinol (THC) was added to produce test solutions containing 0 ng/mL, 100 ng/mL, 200 ng/mL and 1000 ng/mL THC and cyclic voltammetric and linear sweep voltammetric traces were recorded. A boron doped diamond electrode was used in all measurements as the working electrode with a µAUTOLAB potentiostat. A saturated calomel electrode and a platinum wire were used as the reference electrode and counterelectrode respectively.

Figure 2:
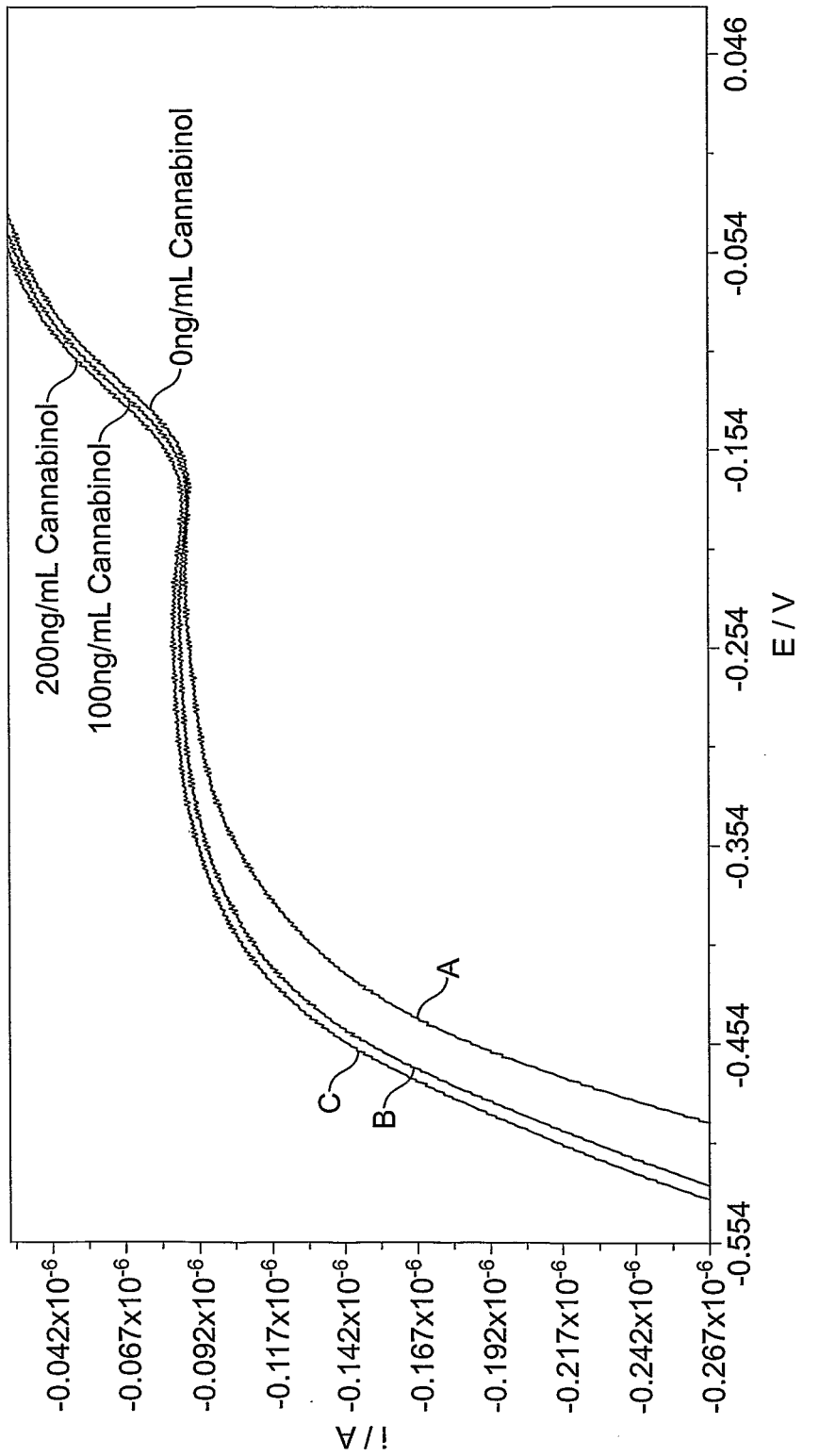
Figure 3:
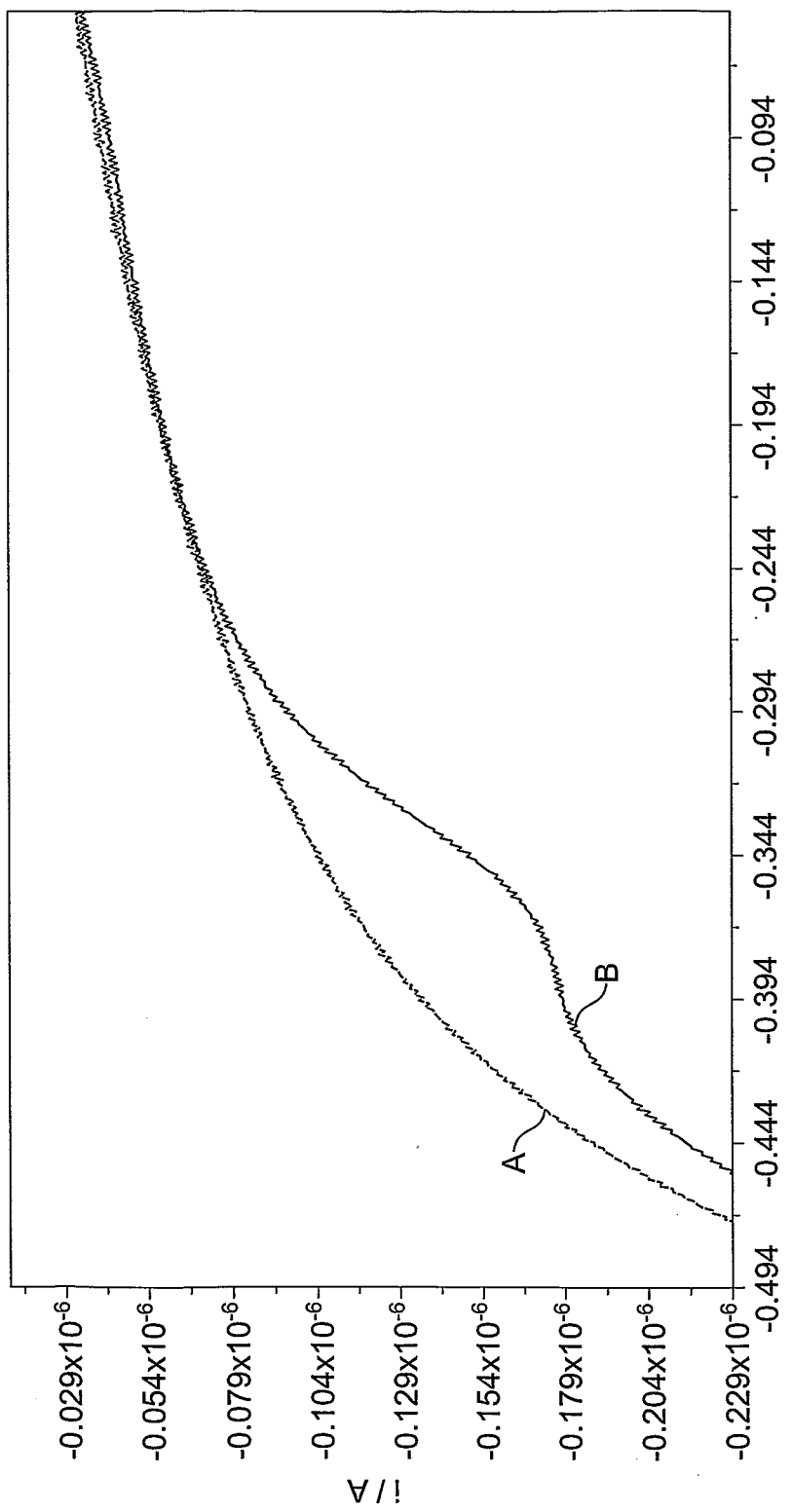

FIG. 2 shows the linear sweep voltammogram for the test solutions at pH 7.0 (curves A, B and C respectively have THC concentrations of 0, 100 and 200 ng/mL). As can be seen, no reaction between THC and 4-AAP was seen. FIG. 3 shows the linear sweep voltammogram for the test solutions at pH 11.0 (curves A and B respectively have THC concentrations of 0 and 1000 ng/mL). A clear response can be seen at ca. −370 mV.

EXAMPLE 2

Detection of epigallocatechin-3-gallate (EGCG)

Using the 4-AAP solutions of Example 1, test solutions containing no EGCG or oversaturated with EGCG were prepared and cyclic voltammetric and linear sweep voltammetric traces were recorded. A boron doped diamond electrode was used in all measurements as the working electrode with a µAUTOLAB potentiostat. A saturated calomel electrode and a platinum wire were used as the reference electrode and counterelectrode respectively.

Figure 4:
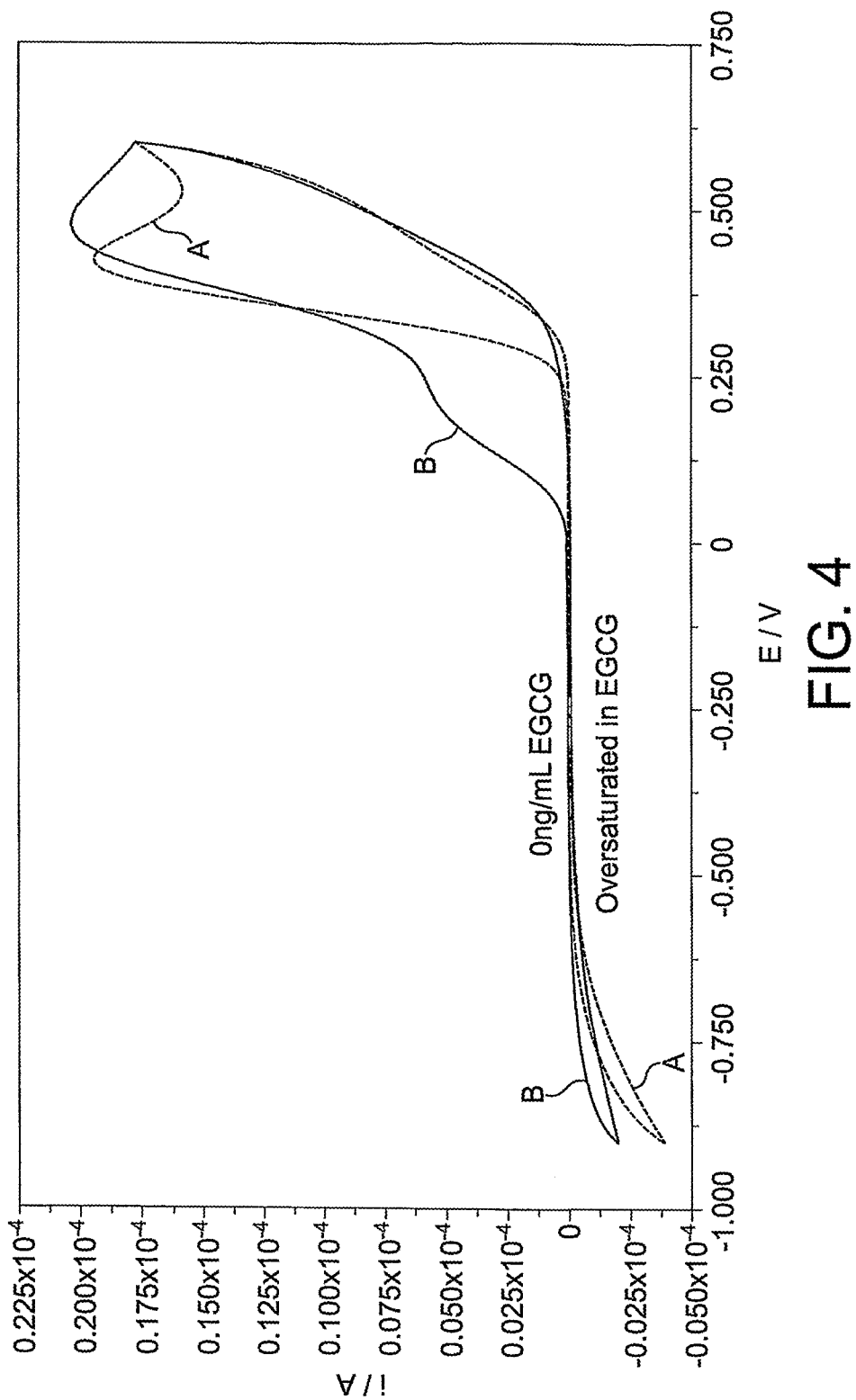
Figure 5:
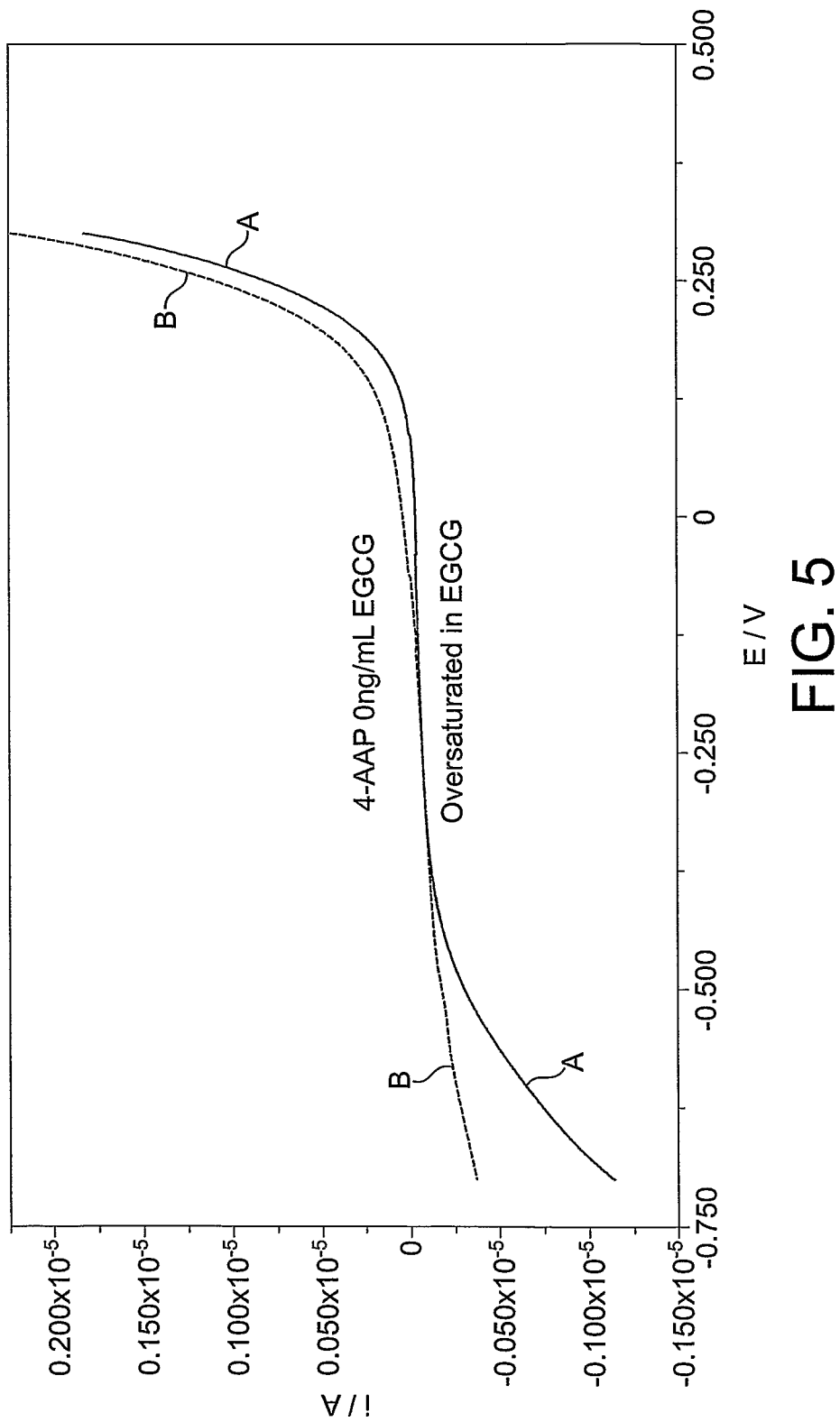

FIG. 4 shows the linear sweep voltammogram for the test solutions at pH 7.0 (curves A and B respectively are for 0 ng/mL EGCG and oversaturated in EGCG). A clear response can be seen at about +0.18 mV. FIG. 5 shows the linear sweep voltammogram for the test solutions at pH 11.0 (curves A and B respectively are for 0 ng/mL EGCG and oversaturated in EGCG). No peaks indicative of reaction between EGCG and 4-AAP are visible.

The invention claimed is:

1. A method of assaying for tetrahydrocannabinol in a body fluid, said method comprising the steps of contacting a sample of body fluid with an imine capable of reacting with tetrahydrocannabinol to yield a quinone imine, and detecting the formation of a quinone imine, wherein said sample is contacted with said imine at a pH of at least 10.5.

2. The method as claimed in claim 1 wherein said imine capable of reacting with tetrahydrocannabinol is a compound of formula I $$R'-N=C^*-(X^*-C^*)_n-C^*-Q-R' \qquad (I)$$

where Q is —O—, —S—, =N— or —NR'—; each R', which may be the same or different, is H or an electron-withdrawing or -donating group; X* is N* or C*; n is 0 or 1; and * indicates that the carbons or nitrogens are part of a delocalised electron system.

3. The method as claimed in claim 1, wherein said imine is formed from an imine precursor.

4. The method as claimed in claim 3, wherein the imine is formed from the imine precursor by oxidation or by application of an electric potential.

5. The method as claimed in claim 3, wherein the imine precursor is an amine of formula (II)

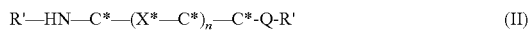  (II)

where Q is —O—, —S—, =N— or —NR'—; each R', which may be the same or different, is H or an electron-withdrawing or -donating group: X* is N* or C*; n is 0 or 1; and * indicates that the carbons or nitrogens are part of a delocalised electron system, or wherein the imine precursor is a cyclic hydrazide.

6. The method as claimed in claim 3, wherein the imine precursor is selected from the group consisting of 1-(substituted-amino)-4-amino benzenes, 1-(substituted-amino)-4-hydroxy benzenes, 1-(substituted-amino)-2-amino benzenes, 1-(substituted-amino)-2-hydroxy benzenes, 1,4-di(substituted-amino)-benzenes, 1,2-di(substituted-amino)-benzenes, 2,3-diaminopyridines, 2,5-diaminopyridines, 3,4-diaminopyridines, 2-amino-3-hydroxypyridines, 4,5-diaminopyrimidines, 4-aminopyrazolones and maleic hydrazides and substituted derivatives thereof.

7. The method as claimed in claim 3, wherein the imine precursor is a 4-amino pyrazolone.

8. The method as claimed in claim 1, wherein the sample is contacted with the imine at a pH of from 10.5 to 12.

9. A method of assaying for a phenol analyte in a body fluid sample, said method comprising contacting said sample with a 4-imino-pyrazolone and electrochemically detecting any resulting quinone imine.

10. The method as claimed in claim 9, wherein the phenol analyte is tetrahydrocannabinol.

* * * * *